United States Patent [19]

Sakagami et al.

[11] Patent Number: 4,524,026
[45] Date of Patent: Jun. 18, 1985

[54] NOVEL PROTEINOUS CANCER-CELL PROLIFERATION INHIBITORY FACTORS

[76] Inventors: Yoshio Sakagami, No. 3-16-19, Jugaoka, Meguro-ku, Tokyo; Hofumi Manabe, No. 2-5-27, Inogashira, Mitaka-shi, Tokyo, both of Japan

[21] Appl. No.: 644,234

[22] Filed: Aug. 27, 1984

[30] Foreign Application Priority Data

Aug. 29, 1983 [JP] Japan ................................ 58-158858
Sep. 1, 1983 [JP] Japan ................................ 58-161237

[51] Int. Cl.$^3$ .................... C07G 7/00; A61K 43/00
[52] U.S. Cl. .................... 260/112 B; 260/112 R; 424/101
[58] Field of Search .................... 260/112 R, 112 B; 424/101, 177

[56] References Cited

U.S. PATENT DOCUMENTS

| | | | |
|---|---|---|---|
| 4,076,701 | 2/1978 | Burton et al. | 260/112 B |
| 4,132,769 | 1/1979 | Osther | 260/112 R X |
| 4,146,603 | 3/1979 | Davidson et al. | 260/112 R X |
| 4,211,766 | 7/1980 | Björklund | 260/112 R X |
| 4,368,148 | 1/1983 | Bottn | 260/112 B |
| 4,447,355 | 5/1984 | Sakamoto et al. | 260/112 B |
| 4,460,694 | 7/1984 | Fletcher | 260/112 B X |

*Primary Examiner*—Howard E. Schain
*Attorney, Agent, or Firm*—Oblon, Fisher, Spivak, McClelland & Maier

[57] ABSTRACT

A new series of cancer-cell proliferation inhibitory factors which inhibit tumor cells, are nontoxic to humans and animals, and show no appreciable effects upon normal cells are disclosed and characterized.

5 Claims, 20 Drawing Figures

NOVEL PROTEINOUS CANCER-CELL PROLIFERATION INHIBITORY FACTORS

This invention relates to novel proteinous substances, namely, cancer-cell proliferation inhibitory factors A, B, C, D, and E, which have been fractionated from human blood or sera and show activities to inhibit the proliferation of malignant tumor cells.

In the course of investigations to find out substances that can inhibit the growth of malignant tumor cells from among proteins isolated from human living bodies, we have discovered a substance which shows inhibitory action against the proliferation of various malignant tumor cells in in-vitro tests and is capable of prolonging the lives of animals with transplanted malignant tumor cells in in-vivo tests.

Named "cancer-cell proliferaton inhibitory factor (T.D.F.H)" by the present inventors because of its peculiar chemical, physical and biological properties, this substance is a new protein isolated from human blood or sera, and shows ability of inhibiting the growth of malignant tumor cells and markedly prolonging the lives of animals to which such cells have been transplanted. Of special note are its specific physiological activities; it has no activity of killing the malignant tumor cells while prominently inhibiting their growth, is nontoxic to humans and animals, and shows no appreciable effects upon normal cells, making this new protein highly valuable as a medicine.

The novel proteinous cancer-cell proliferation inhibitory factor of this invention (T.D.F.H) can be isolated from human blood or sera by a proper combination of known oerations, such as salting out, extraction, adsorption, elution, dialysis, fractionation, precipitation, filtration, isoelectric precipitation, gel filtration, ion-exchange resin treatemnt and electrophoresis.

More specifically, crude powder of T.D.F.H can be obtained by adding, to human blood or serum, ammonium sulfate, sodium chloride, acetone or alcohol to cause precipitation of the effective component, followed by purification through dialysis and drying.

Further purification can be achieved by column chromatography on ion-exchange resins, Sephadex, activated charcoal, silica gel or DEAE-cellulose, electrophoresis on polyacrylamide gel, sucrose or the like, and isoelectric precipitation, alone or in combination. It is also possible to purify T.D.F.H by adsorption on silica gel, bentonite, acid clay, activated charcoal or other suitable adsorbents.

T.D.F.H, thus isolated from human blood or serum has specific physiological activities as described above, and is useful as an anticancer agent.

Further studies have revealed that this proteinous cancer-cell proliferation inhibitory factor is not a single substance, but is a mixture of several substances that can be separated from one another, each component having ability of inhibiting the growth of malignant tumor cells. The individual components separated were then named cancer-cell proliferation inhibitory factors A, B and C (T.D.F.H.A, T.D.F.H.B and T.D.F.H.C), respectively.

These factors can be separated from one another if the salting-out operation mentioned above is performed at different degrees of alcohol saturation, for example, 40%, 50% and 60%, depending on their molecular weights, and each precipitate, after confirmation of its purity by adsorption and elution with molecular sieves, is carefully fractionated by means of column chromatography.

Cancer-cell Proliferation Inhibitory Factor A (T.D.F.H.A)

Figure 1:
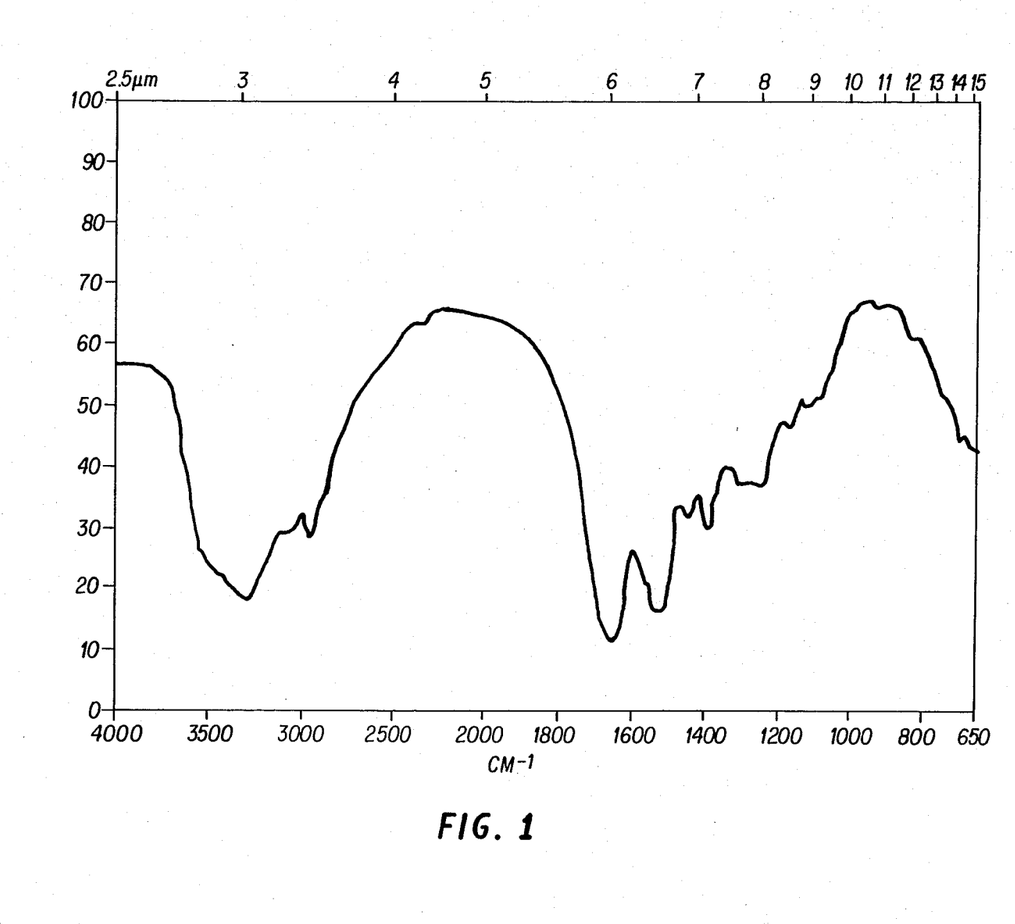
FIG. 1 is the infrared absorption spectrum of T.D.F.H.A of this invention.
Figure 2:
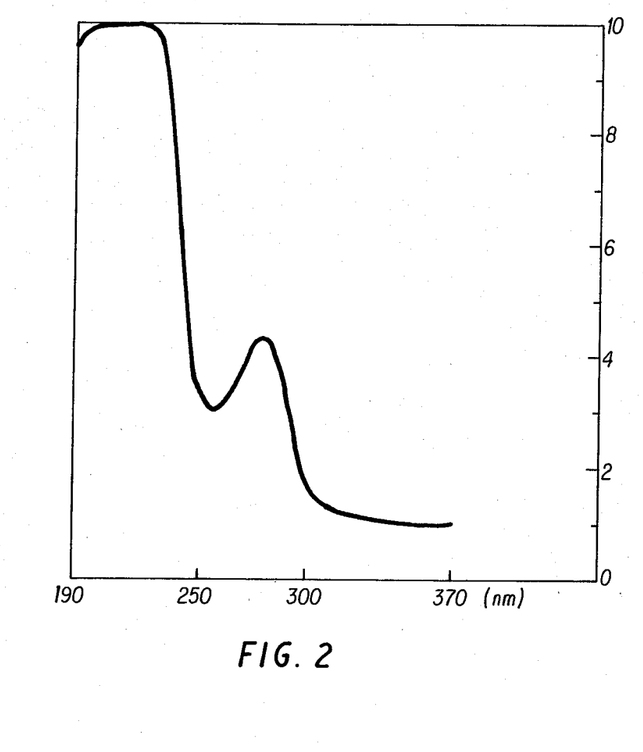
FIGS. 2, 3 and 4 show its ultraviolet absorption spectra at pH 3.0, 7.0 and 10.0, respectively.
Figure 3:
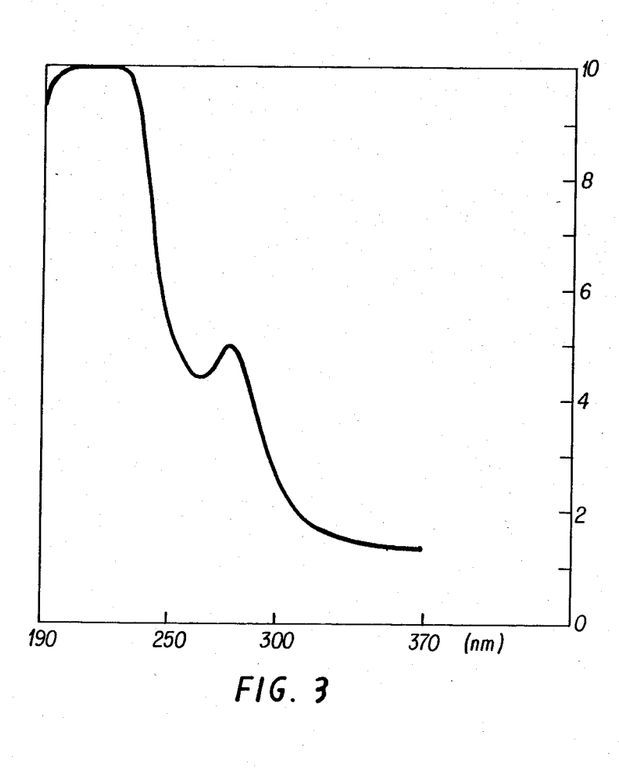
Figure 4:
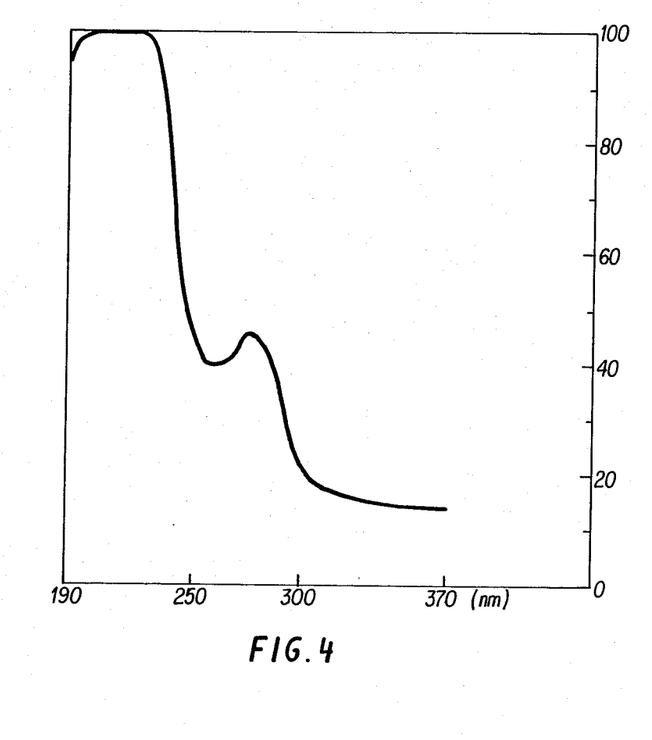

Appearance: White powder
Melting point: 245°–259° C. (dec)
Structure: Glycoprotein
Molecular weight: Approximately 73,900 (when measured by electrophoresis in 10% sodium dodecyl sulfate solution)
Solubility: Readily soluble in water; insoluble in butanol, acetone, ethyl acetate, chlorform, benzene and hexane
Amino acid composition: 10.0% aspartic acid, 5.4% threonine, 3.8% serine, 16.0% glutamic acid, 4.2% proline, 1.4% glycine, 4.8% alanine, 2.6% cystine, 5.1% valine, 0.8% methionine 2.2% isoleucine, 9.6% leucine, 4.9% tyrosine, 5.7% phenylalanine, 11.4% lysine, 3.5% histidine and 5.2% arginine
Color reaction: Positive response to the ninhydrin, anthrone, Molish and periodic acid reactions
Infrared absorption spectrum: Refer to FIG. 1 (measured on KBr pellet).
Ultraviolet absorption spectra: Refer to FIGS. 2, 3 and 4.
  Absorption maximum at 279 nm in water of pH 3.0 (FIG. 2)
  Absorption maximum at 278 nm in water of pH 7.0 (FIG. 3)
  Absorption maximum at 277 nm in water of pH 10.0 (FIG. 4)

Cancer-cell Proliferation Inhibitory Factor B (T.D.F.H.B.)

Figure 5:
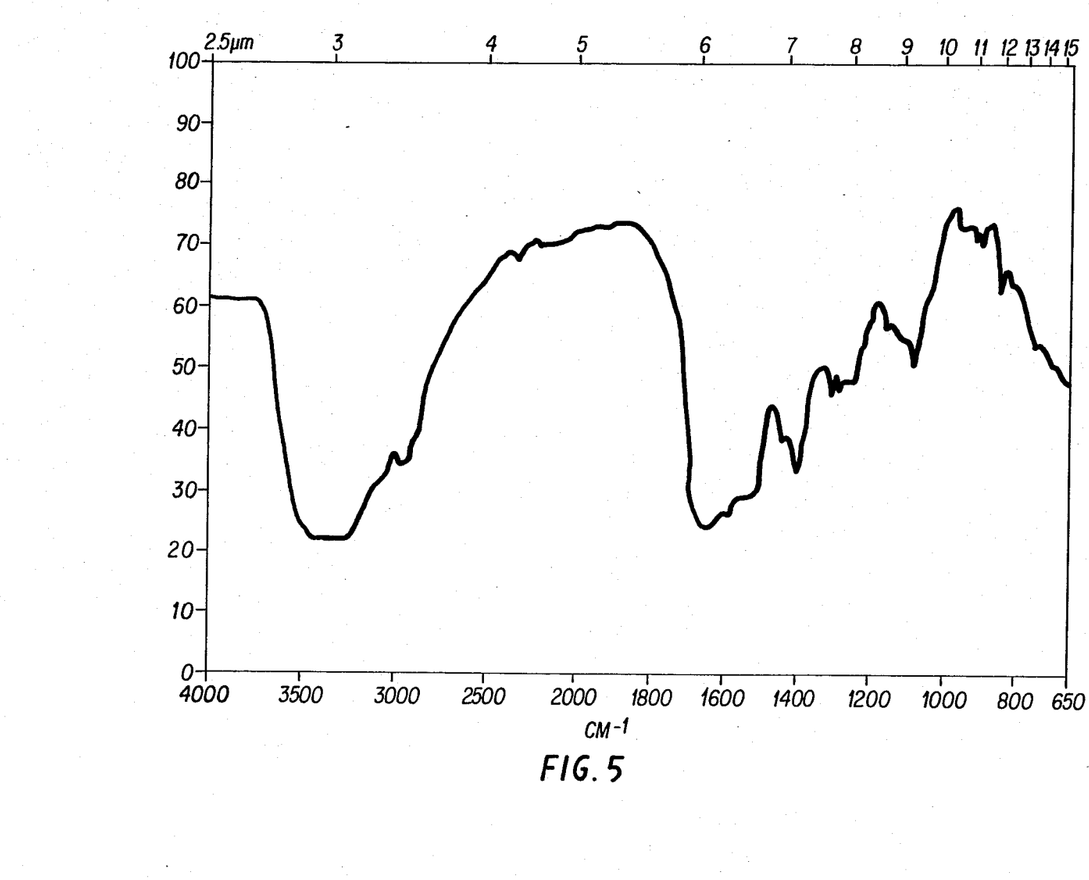
FIG. 5 is the infrared absorption spectrum of T.D.F.H.B of this invention.
Figure 6:
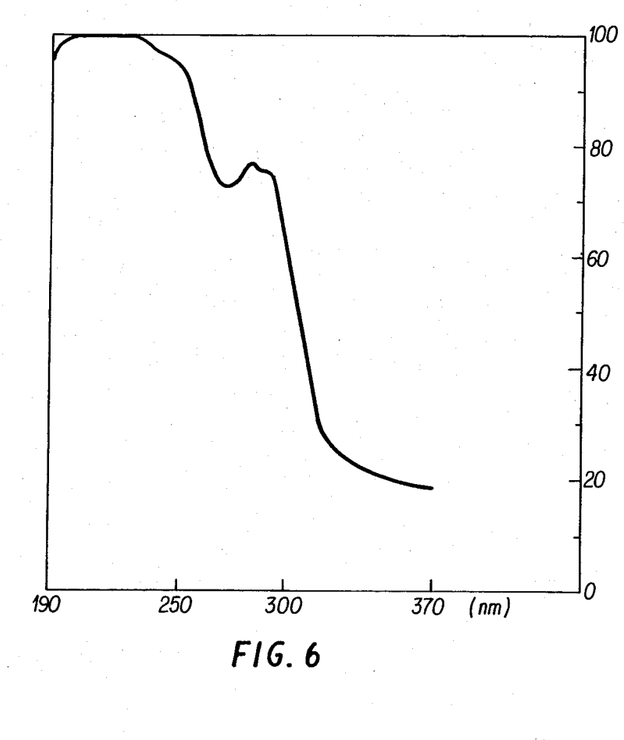
FIGS. 6, 7 and 8 show its ultraviolet absorption spectra at pH 3.0, 7.0 and 10.0, respectively.
Figure 7:
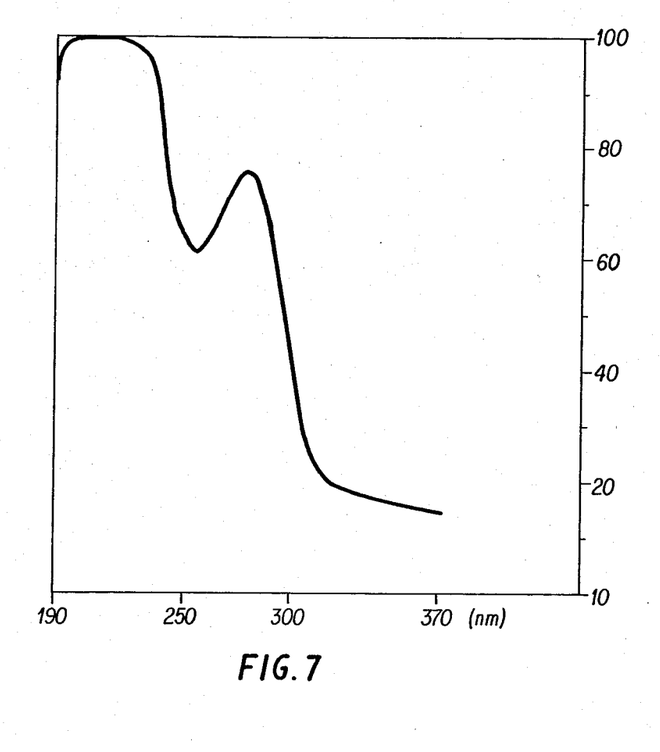
Figure 8:
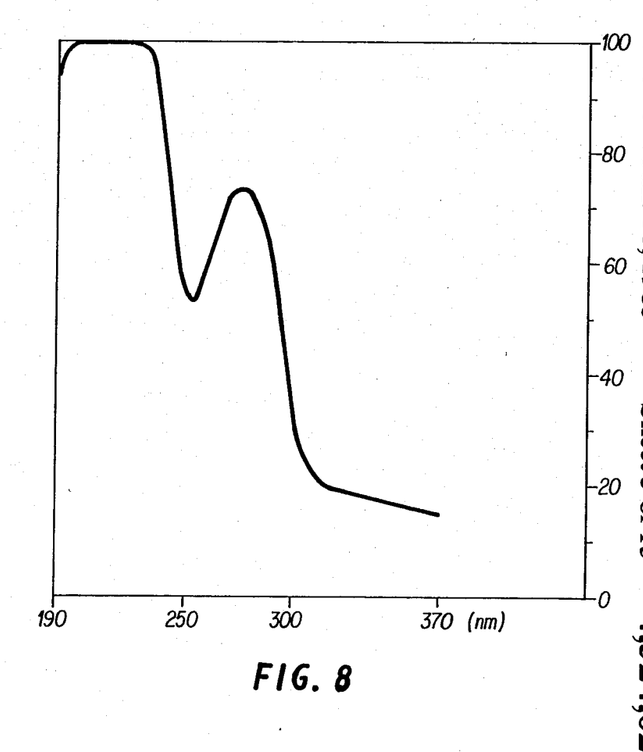

Appearance: White powder
Melting point: 221°–225° C. (dec)
Structure: Protein
Molecular weight: Approximately 22,100 (when measured by electrophoresis in 10% sodium dodecyl sulfate solution)
Solubility: Readily soluble in water; insoluble in acetone, ethyl acetate, chlorform, benzene and hexane
Amino acid composition: 16.0% aspartic acid, 5.2% threonine, 5.8% serine, 6.9% glutamic acid, 2.3% proline, 4.1% glycine, 5.9% alanine, 2.3% cystine, 4.4% valine, 1.7% methionine, 4.2% isoleucine, 7.9% leucine, 4.0% tyrosine, 3.9% phenylalanine, 7.7% lysine, 1.6% histidine and 11.6% arginine
Color reaction: Positive response to the ninhydrin reaction, and negative response to the anthrone, Molish and periodic acid reactions
Infrared absorption spectrum: Refer to FIG. 5 (measured on KBr pellet).
Ultraviolet absorption spectra:
  Absorption maxima at 283 nm and 290 nm in water of pH 3.0 (FIG. 6)
  Absorption maximum at 280 nm in water of pH 7.0 (FIG. 7)
  Absorption maximum at 277 nm in water of pH 10.0 (FIG. 8)

Cancer-cell Proliferation Inhibitory Factor C (T.D.F.H.C)

Appearance: White powder
Melting point: 237°–240° C. (dec)
Structure: Protein

Molecular weight: Approximately 14,000 (when measured by electrophoresis in 10% sodium dodecyl sulfate solution)

Figure 9:
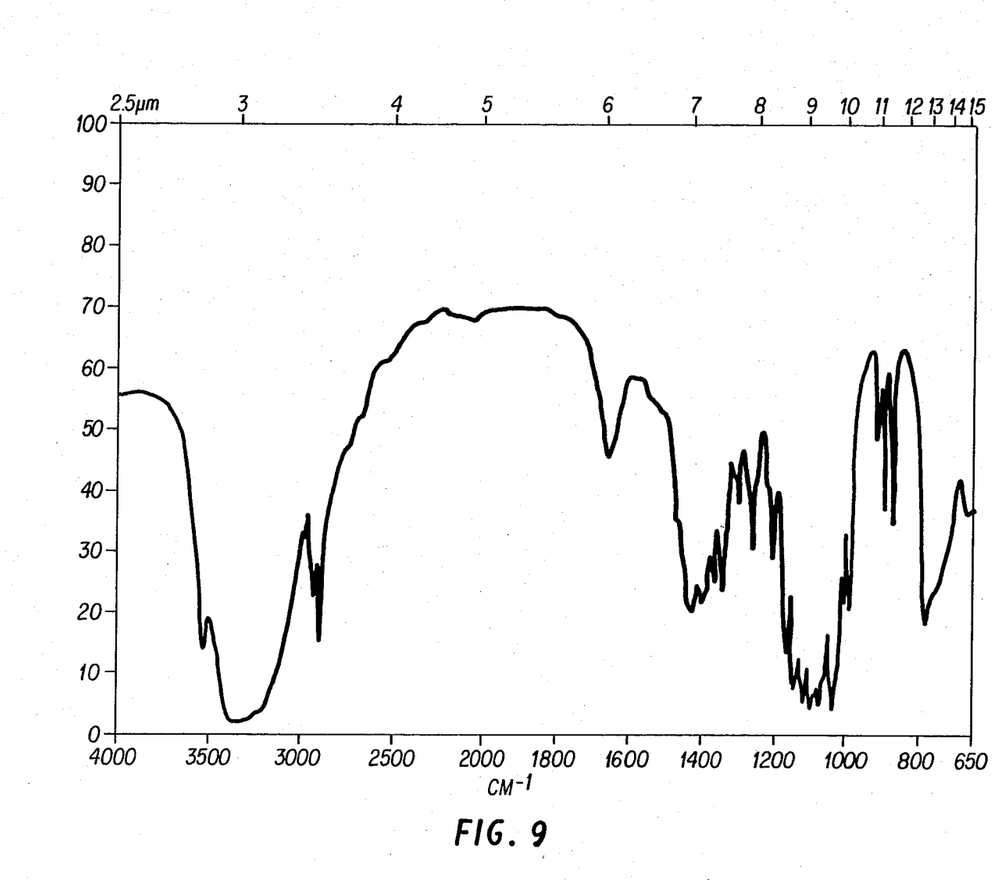
FIG. 9 is the infrared absorption spectrum of T.D.F.H.C of this invention.

Solubility: Readily soluble in water; insoluble in acetone, ethyl acetate, chlorform, benzene and hexane Amino acid composition: 18.0% aspartic acid, 5.4% threonine, 6.4% serine, 5.2% glutamic acid, 1.7% proline, 5.1% glycine, 6.4% alanine, 2.1% cysteine, 4.3% valine, 1.9% methionine, 4.5% isoleucine, 6.8% leucine, 3.6% tyrosine, 3.0% phenylalanine, 6.0% lysine, 1.1% histidine and 11.6% arginine Color reaction: Positive response to the ninhydrin reaction, and negative response to the anthrone, Molish and periodic acid reactions Infrared absorption spectrum: Refer to FIG. 9 (measured on KBr pellet).

Figure 10:
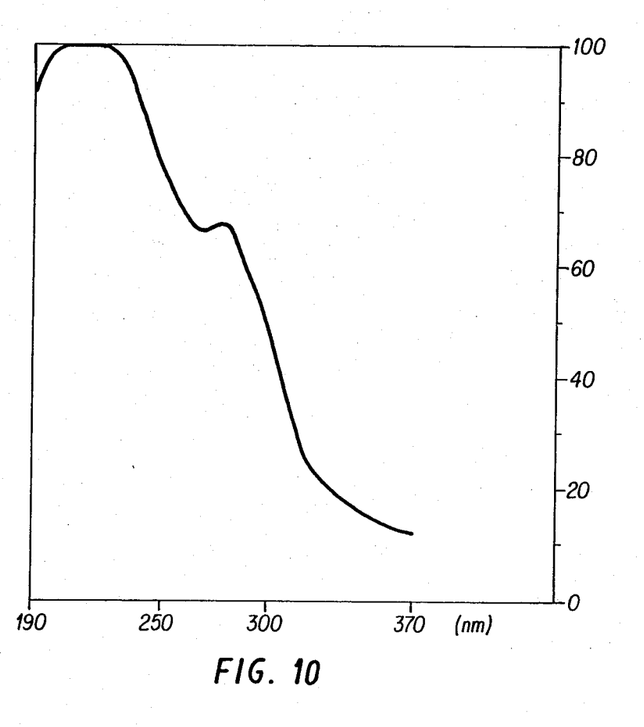
FIGS. 10, 11 and 12 show its ultraviolet absorption spectrum at pH 3.0, 7.0
Figure 11:
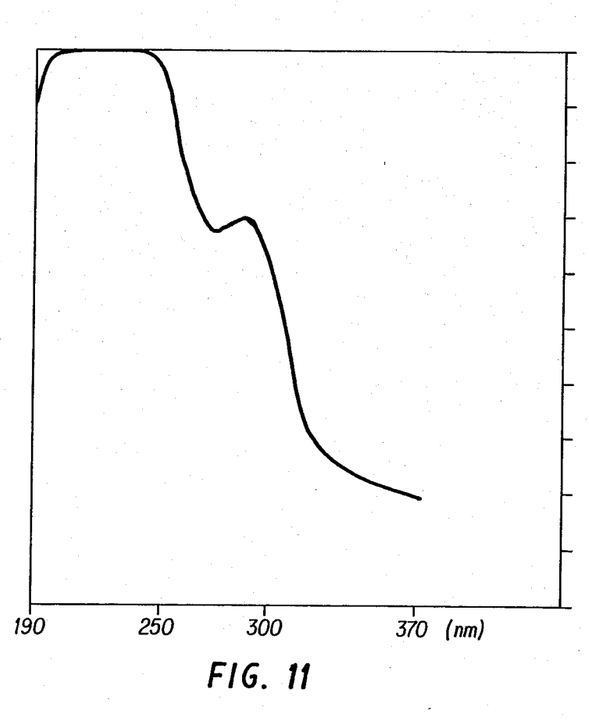
Figure 12:
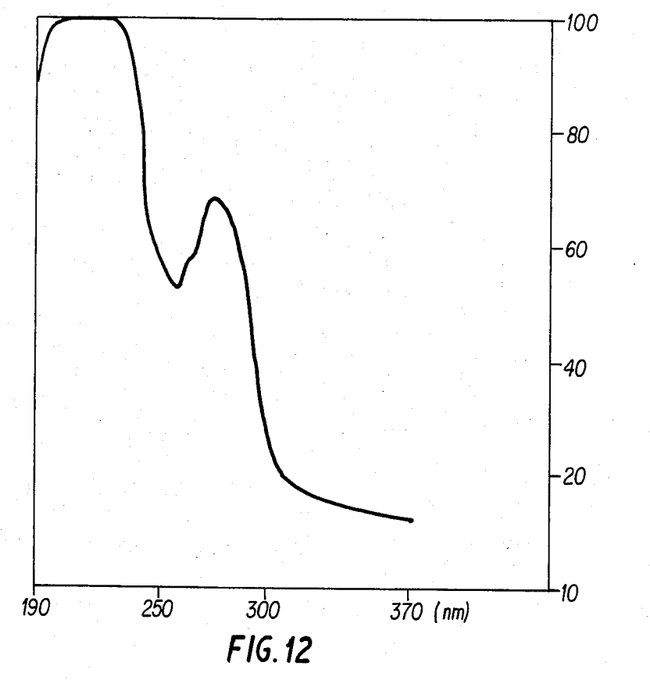

Ultraviolet absorption spectra:
Absorption maximum at 278 nm in water of pH 3.0 (FIG. 10)
Absorption maximum at 290 nm in water of pH 7.0 (FIG. 11)
Absorption maximum at 277 nm in water of pH 10.0 (FIG. 12)

When subjected to electrophoresis on 7% polyacrylamide gel, T.D.F.H.A, T.D.F.H.B. and T.D.F.H.C. each migrate from the origin point at ph 8.0, 9.5 and 10.0 respectively, forming a single band.

Named "cancer-cell killing and proliferation inhibiting factor (T.C.F.H)" by the present inventors because of its peculiar chemical, physical and biological properties, this substance is a new protein isolated from human blood, and shows ability of inhibiting the growth of malignant tumor cells and markedly prolonging the lives of animals to which such cells have been transplanted. Of special note are its specific physiological activities; it has prominent actions to kill malignant tumor cells or to inhibit their growth, is nontoxic to humans and animals, and shows no appreciable effects upon normal cells, making this new protein highly valuable as a medicine.

The novel proteinous cancer-cell killing and proliferation inhibiting factor of this invention (T.C.F.H) can be isolated form human blood by a proper combination of known operations, such as salting out, ectraction, adsorption, elution, dialysis, fractionation, precipitation, filtration, isoelectric precipitation, gel filtration, ion-exchange resin treatment and electrophoresis. More specifically, crude powder of T.C.F.H can be obtained by adding, to human blood or clot extracts, ammonium sulfate, sodium chloride, alcohol or the like to cause precipitation of the effective component, followed by purification through dialysis and drying.

Further purification can be achieved by column chromatography on ion-exchange resins, Sephadex, activated charcoal, silica gel, cellulose or DEAE-cellulose, electrophoresis on polyacrylamide gel, sucrose or the like, isoelectric precipitation and ultrafiltration, alone or in combination. It is also possible to purify T.C.F.H by adsorption on silica gel, bentonite, acid clay, activated charcoal or other suitable adsorbents.

T.C.F.H, thus isolated from human blood or clot has specific physiological activities as described above, and is useful as an anticancer agent.

Further studies have revealed that this proteinous cancer-cell killing and proliferation inhibiting factor is not a single substance, but is a mixture of several substances that can be separated from one another, each component having ability of inhibiting the growth of malignant tumor cells. The individual components separated were then named cancer-cell killing and proliferation inhibiting factors D and E (T.C.F.H.A and T.C.F.H.B), respectively.

These factors can be separated from one another if the salting-out operation mentioned above is performed at different degrees of salt saturation depending on their molecular weights, and each precipitate, after confirmation of its purity by adsorption and elution with molecular sieves, is carefully fractionated by means of column chromatography.

Cancer-cell Killing and Proliferation Inhibiting Factor D (T.C.F.H.D.)

Appearance: White powder

Melting point: 218°–221° C. (dec)

Structure: Protein

Molecular weight: Approximately 40,000 (when measured by electrophoresis in 10% sodium dodecyl sulfate solution)

Figure 13:
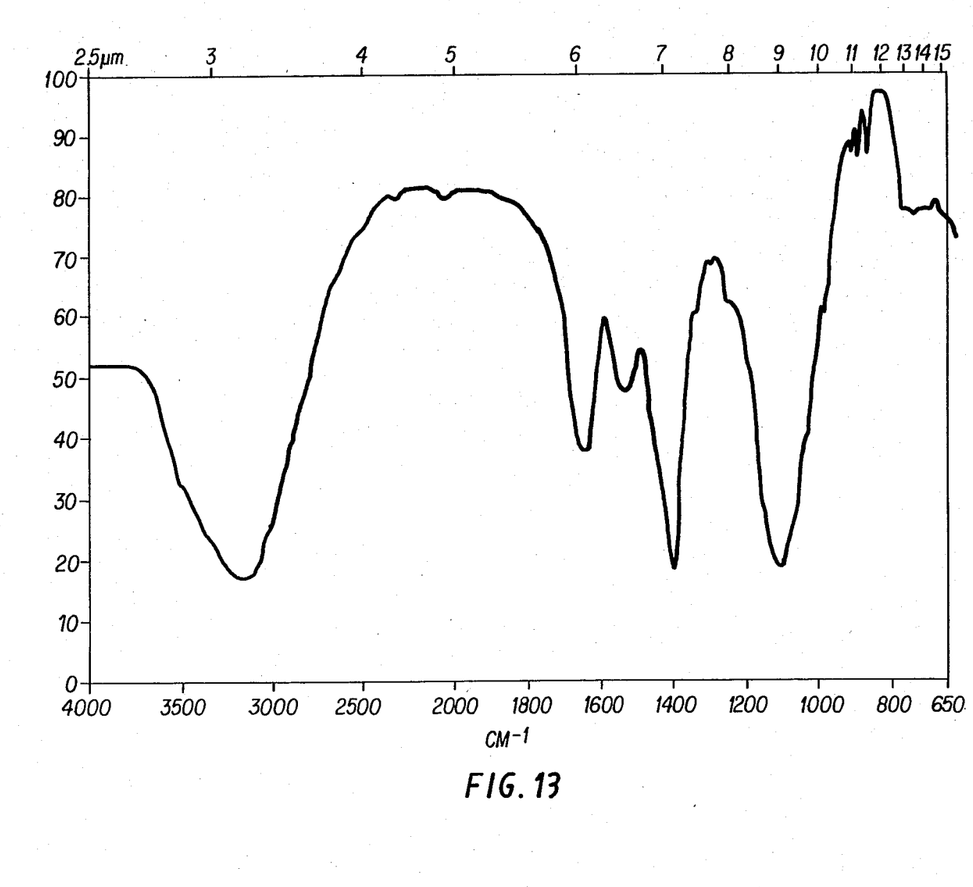
FIG. 13 is the infrared absorption spectrum of T.C.F.H.D of this invention.

Solubility: Readily soluble in water; insoluble in butanol, acetone, ethyl acetate, chlorform, benzene and hexane Amino acid composition: 8.9% aspartic acid, 5.7% threonine, 4.3% serine, 6.3% glutamic acid, 3.8% proline, 5.8% glycine, 5.8% alanine, 0.6% cysteine, 5.2% valine, 0.5% methionine, 2.2% isoleucine, 4.7% leucine 3.0% tyrosine, 2.6% phenylalanine 2.4% lysine, 1.3% histidine and 4.4% arginine Color reaction: Positive response to the ninhydrin reaction, and negative response to the anthrone, Molish and periodic acid reactions Infrared absorption spectrum: Refer to FIG. 13(measured on KBr pellet).

Figure 14:
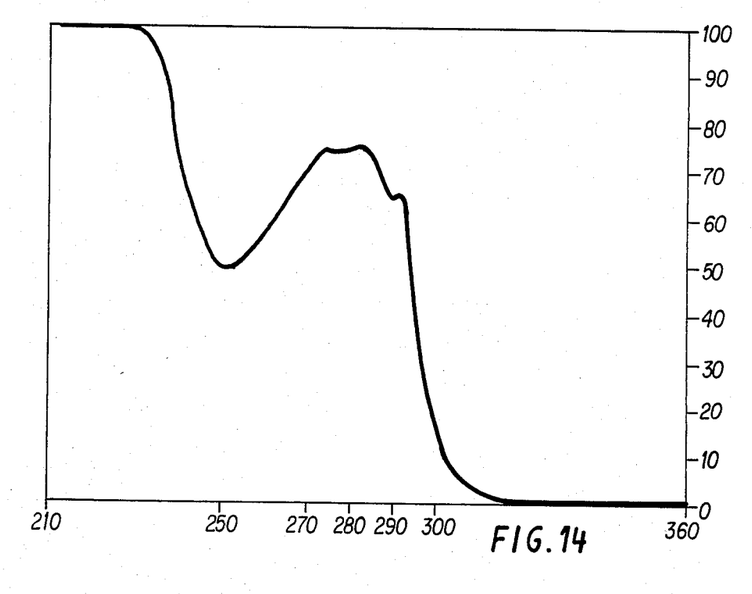
FIGS. 14, 15 and 16 show its ultraviolet absorption spectra at pH 5.0, 7.0 and 10.0, respectively.
Figure 15:
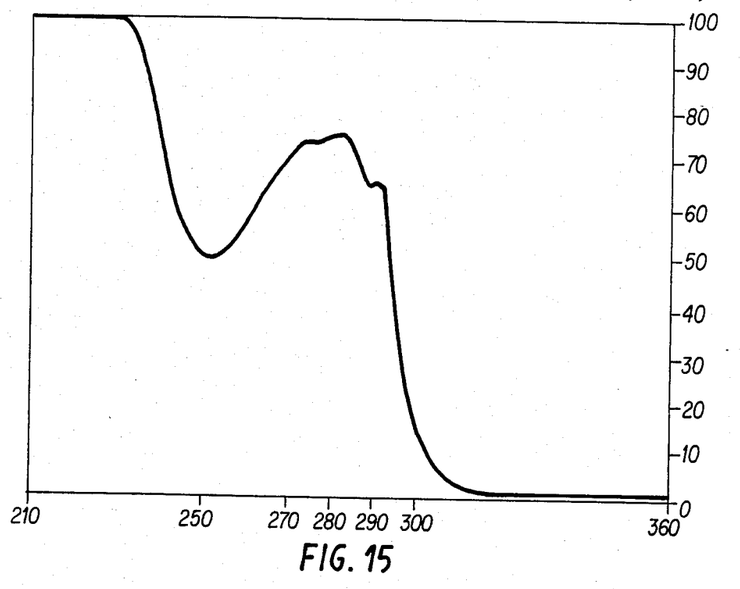
Figure 16:
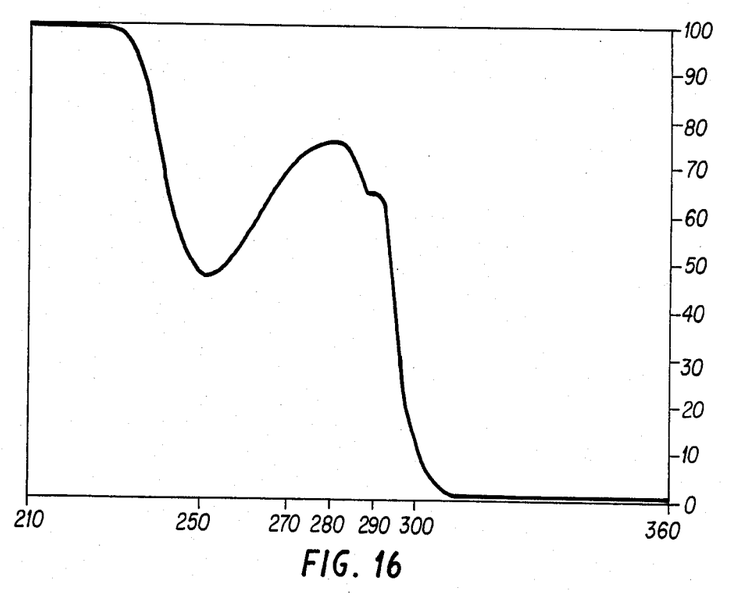

Ultraviolet absorption spectra:
Absorption maxima at 275 nm, 282.5 nm and 291.5 nm in water of pH 5.0 (FIG. 14)
Absorption maxima at 275 nm, 282.5 nm and 291.5 nm in water of pH 7.0 (FIG. 15)
Absorption maxima at 282 nm and 291.5 nm in water of pH 10.0 (FIG. 16)

Cancer-cell Killing and Proliferation Inhibiting Factor E (T.C.F.H.E)

Appearance: White powder

Melting point: 231°–233° C. (dec)

Structure: Protein

Molecular weight: Approximately 44,000 (when measured by electrophoresis in 10% sodium dodecyl sulfate solution)

Figure 17:
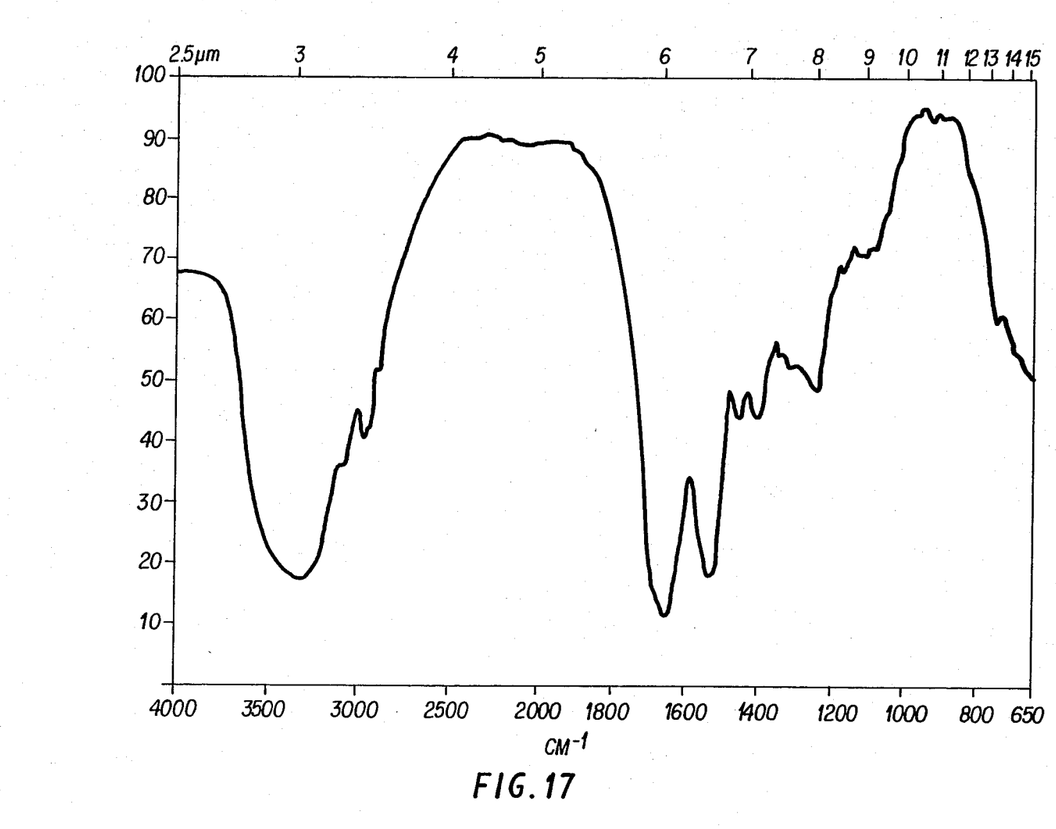
FIG. 17 is the infrared absorption spectrum of T.C.F.H.E of this invention.

Solubility: Readily soluble in water; insoluble in butanol, acetone, ethyl acetate, chlorform, benzene and hexane Amino acid composition: 9.2% aspartic acid, 5.7% threonine, 4.3% serine, 8.6% glutamic acid, 4.0% proline, 4.7% glycine, 5.6% alanine, 1.0% cysteine, 5.2% valine, 0.6% methionine, 2.2% isoleucine, 6.0% leucine 3.4% tyrosine, 3.1% phenylalanine , 4.4% lysine, 1.9% histidine and 4.7% arginine Color reaction: Positive response to the ninhydrin reaction, and negative response to the anthrone, Molish and periodic acid reactions Infrared absorption spectrum: Refer to FIG. 17(measured on KBr pellet).

Figure 18:
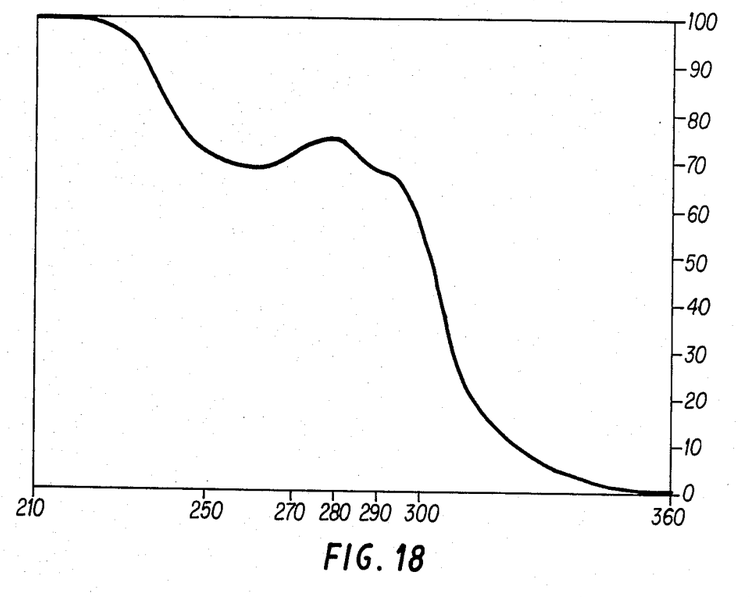
FIGS. 18, 19 and 20 show its ultraviolet absorption spectra at pH 5.0, 7.0 and 10.0, respectively.

Ultraviolet absorption spectra:
Absorption maximum at 280 nm with a shoulder at 294 nm in water of pH 5.0 (FIG. 18)

Figure 19:
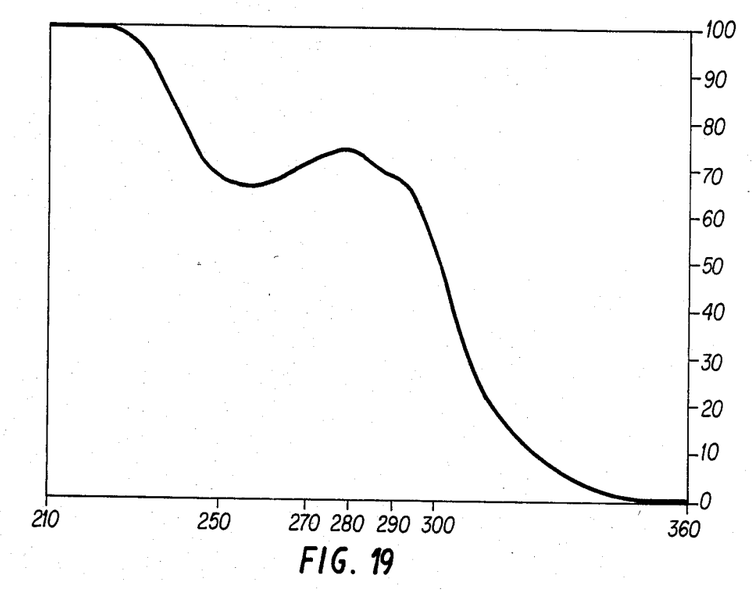

Absorption maximum at 280 nm with a shoulder at 291 nm in water of pH 7.0 (FIG. 19)

Figure 20:
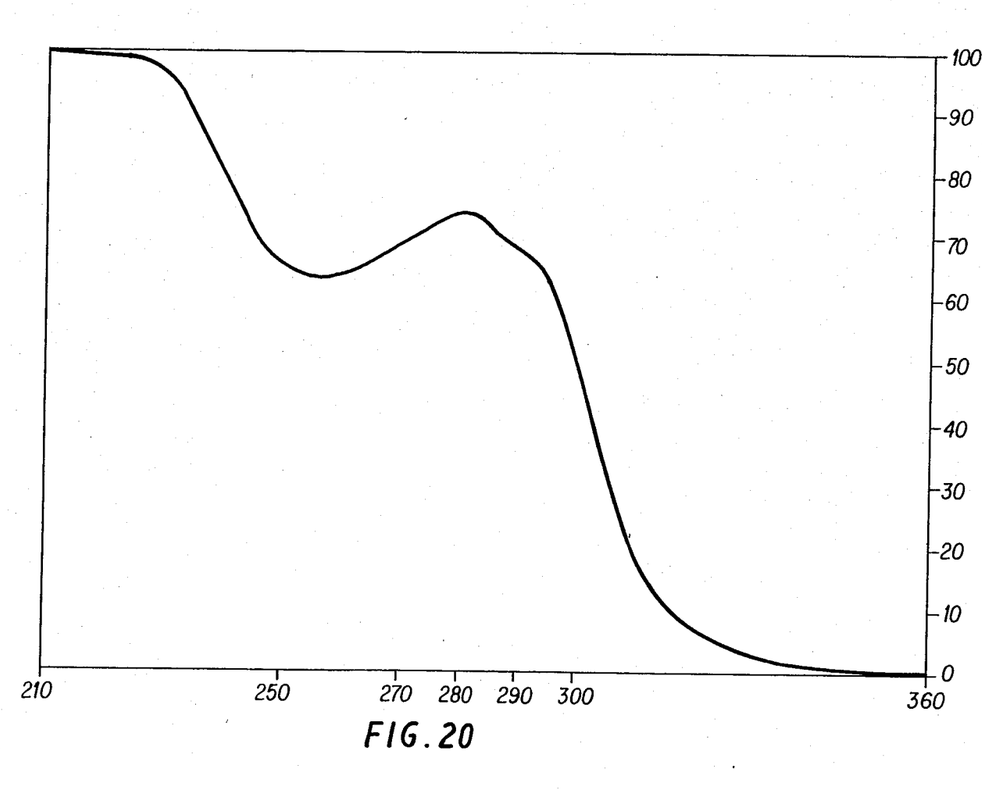

Absorption maximum at 281 nm with a shoulder at 293 nm in water of pH 10.0 (FIG. 20)

When subjected to electrophoresis on 7% polyacrylamide gel, T.C.F.H.A and T.C.F.H.B migrate from the origin point at pH 6.0, each forming a single band.

It is therefore possible to separate them from one another by using this method in place of column chromatography. The factors thus purified, as well as crude powder obtained in preceding purification steps, can be used as medicines to inhibit the proliferation of various malignant tumor cells.

These may also be used in a variety of dosage forms, such as parenteral injections.

The following examples will further illustrate the present invention.

EXAMPLE 1

Two liters of acetone was added to one liter of human serum at −20° C., and the precipitate collected by centrifugation was dissolved in as little distilled water as possible. Fractional precipitation by addition of ethanol to a concentration of 45 to 50% gave 8.6 g of solid.

Five grams of this precipitate was adsorbed on 20 ml Sephadex G-200 at pH 7.3, which was follwed by elution with 30 ml of 0.05 M Tris-HCl buffer solution (pH: 7.3), affording 0.9 g of crude T.D.F.H.A.

This was then adsorbed on DEAE-cellulose (Whatman), and eluted with 40 ml of sodium chloride solution (concentration gradient: 0 to 0.5 M) to give seven fractions roughly separated. The fifth fraction was dialyzed with 0.02 M Tris buffer solution, desalted and freeze-dried, yielding 23.7 mg of crude product.

This crude product (50 mg) was again adsorbed on DEAE-cellulose (Whatman), eluted with 0.1 M sodium chloride solution at pH gradient from 8.0 to 5.0 to give five fractions, and the second fraction was desalted and freeze-dried to afford 7.3 mg of T.D.F.H.A.

This was further subjected to electrophoresis on 7% polyacrylamide gel for four hours, and the second band which showed a positive response to the ninhydrine test was eluted with 0.02 M Tris buffer solution, followed by dialysis and drying. The resulting T.D.F.H.A (0.6 mg) showed a single band in electrophoresis.

Tissue culture tests showed that the rate of inhibition against the growth of leukemia L1210 cells by this substance is 99% and 61.5% at concentrations of 0.01 mg/ml and 0.001 mg/ml, respectively.

EXAMPLE 2

The fifth fraction obtained, in the same manner as Example 1, from the first chromatogrphy on DEAE-cellulose (31.2 mg) was subjected to electrophoresis on polyacrylamide amide gel at pH 9.5 to isolate the effective component as a single substance. Dialysis followed by freeze drying gave 0.6 mg of purified T.D.F.H .A as white powder.

EXAMPLE 3

Eight liters of human serum was treated with ethanol (60% of the serum), the precipitate was removed, and ethanol was added to the supernatant to a concentration of 70%. The resulting precipitate was adsorbed on 40 ml Sephadex G-50 at pH 7.3, and eluted with 50 ml of Tris-HCl buffer solution (pH: 7.3), affording 5.8 g of crude T.D.F.H.B.

This was then adsorbed on DEAE-cellulose (Whatman), and eluted with 50 ml of Tris-HCl buffer solution (pH 7.0; ion strength gradient: 0.02 to 0.05M) to give six fractions.

Dialysis, desalting and freeze drying of the first fraction gave 25.4 mg of crude product.

This was further adsorbed on DEAE-cellulose (Whatman), eluted with 0.1 M sodium chloride solution (pH gradient: 8.0 to 5.0) to give six fractions, and the first fraction was dialyzed, desalted and freeze-dried, yielding 4.2 mg of purified T.D.F.H.B as white powder.

This substance showed a single band in electrophoresis. Tissue culture tests showed that addition of this substance (400 mcg/ml) reduced the angle of growth curve for leukemia L1210 cells by about 20 degrees.

EXAMPLE 4

Two liters of human serum was treated with ethanol in the same manner as Example 3, the precipitate was adsorbed on DEAE-cellulose (Whatman), and eluted with 0.1 M sodium chloride solution (pH gradient: 8.0 to 5.0) to give six fractions. The first fraction was desalted by dialysis, freeze-dried, and subjected to electrophoresis on 7% polyacrylamide gel to isolate the effective component as a single substance. T.D.F.H.B (85 mcg) was thus obtained as white powder after dialysis and freeze drying.

Tissue culture tests similar to Example 3 showed that this substance is also effective in reducing the angle of growth curve for leukemia L1210 cells.

EXAMPLE 5

Eight liters of human serum was treated with ethanol (70% of the serum), the precipitate was removed, and the supernatant was concentrated under reduced pressure and freezedried. This solid was adsorbed on 40 ml Sephadex G-50 at pH 7.3, and eluted with 30 ml of 0.05 M Tris-HCl buffer solution (pH: 7.3), affording about 1.0 g of crude T.D.F.H.C.

This was then adsorbed on DEAE-cellulose (Whatman), and eluted with 50 ml of Tris-HCl buffer solution (pH 7.0; ion strength gradient: 0.02 to 0.05 M) to give three fractions.

Dialysis, desalting and freeze drying of the second fraction gave 14.5 mg of crude product.

This was further adsorbed on DEAE-cellulose (Whatman), eluted with 0.1 M sodium chloride solution (pH gradient: 8.0 to 5.0) to give six fractions, and the fourth fraction was desalted by dialysis and freeze-dried, yielding 1.8 mg of purified T.D.F.H.C as white powder.

This substance showed a single band in electrophoresis. Tissue culture tests showed that addition of this substance (500 mcg/ml) reduced the angle of growth curve for leukemia L1210 cells by about 10 degrees.

EXAMPLE 6

Two liters of human serum was treated in the same manner as Example 5, the freeze-dried product obtained from the supernatant was adsorbed on DEAE-cellulose (Whatman), and eluted with 0.1 M sodium chloride solution (pH gradient: 8.0 to 5.0) to give six fractions. The fourth fraction was desalted by dialysis, freeze-dried, and subjected to electrophoresis on polyacrylamide gel to isolate the effective component as a single substance. T.D.F.H.C (184 mcg) was thus obtained as white powder after dialysis and freeze drying.

Tissue culture tests similar to Example 5 showed that this substance is also effective in reducing the angle of growth curve for leukemia L1210 cells.

EXAMPLE 7

Tissue culture tests were conducted to determine the effect to inhibit the proliferation of various malignant tumor cells, for the T.D.F.H.A samples obtained in Examples 1 and 2 (at 500 mcg/ml concentration).

The inhibition rate was 32.6% for leukemia L5178 cells, 21.3% for sarcoma S180 cells, and 32.3% for Ehrlich's carcinoma cells, but no such inhibitory effect was observed for the primary tissue-cultured cells of rats liver. Subsequent staining revealed that all the tested malignant tumor cells remained alive.

EXAMPLE 8

An animal test was carried out for T.D.F.H.A obtained in Example 1 using four groups of male BDF mice (weighing 20.0 g), each group consisting of five mice.

In the first group, 0.1 mg of T.D.F.H.A was abdominally administered to each mouse 24 hours after abdominal transplantation of leukemia L1210 cells ($1 \times 10^6$). Similarly, 0.01 mg and 0.001 mg of the sample was administered in the second and third groups.

The average life time was 9.7 days for the control group, 20.0 days for the first test group, 15.7 days for the second and 12.3 days for the third, the T/c value being 207, 162 and 128 percent for the first, second and third groups, respectively.

EXAMPLE 9

Tissue culture tests showed that T.D.F.H.B obtained in Example 3 (at 500 mcg/ml concentration) reduced the angle of growth curves for leukemia L5178Y cells, sarcoma S180 cells and Ehrlich's carcinoma cells by about 15 degrees, 14 degrees and 5 degrees, respectively.

On the other hand, no such inhibitory effect was observed for the primary tissue-cultured cells of rat liver.

Subsequent staining demonstrated that all the malignant tumor cells tested remained alive after the test.

EXAMPLE 10

Tissue culture tests showed that T.D.F.H.C obtained in Example 5 and 6 (at 500 mcg/ml concentration) reduced the angle of growth curves for leukemia L5178Y cells, sarcoma S180 cells and Ehrlich's carcinoma cells by 1 degree, about 22 degrees and 1 degree, respectively.

On the other hand, no such inhibitory effect was observed for the primary tissue-cultured cells of rat liver.

Subsequent staining demonstrated that all the malignant tumor cells tested remained alive after the test.

EXAMPLE 11

Water-soluble component (8.4 g) obtained from human clot was dissolved in water, and ethanol was added to the solution to a saturation degree of 65 to 70% to cause precipitation, giving about 700 mg of crude T.C.F.H.

Tissue culture tests on leukemia L1210 cells using this substance showed that the relative survival rate (based on a control culture sample) after five days was 64%, 79% and 90% at concentrations of 1 mg/ml, 0.1 mg/ml and 0.01 mg/ml, respectively, the relative activity to inhibit the cell growth being 36%, 21% and 10%.

EXAMPLE 12

The substance obtained in the same way as Example 11 (350 mg) was adsrobed on 30 ml of Sephadex G-100 at pH 7.0, and eluted with 30 ml of 0.05 M Tris-HCl buffer solution, affording about 60 mg of crude T.C.F.H.

Similar tissue culture tests as Example 11 showed that the relative survival rate of leukemia L1210 cells was 34% after five days at a concentration of 0.1 mg/ml, the relative activity to inhibit the cell growth being 64%.

EXAMPLE 13

Water-soluble component (2.1 g) obtained from human clot was dissolved in water, and ammonium sulfate was added to the solution to a saturation degree of 80% to cause precipitation, giving about 600 mg of crude T.C.F.H.

Tissue culture tests on sarcoma 180 cells using this substance showed that the relative survival rate (based on a control culture sample) after five days was 49%, 61% and 73% at concentrations of 1 mg/ml, 0.1 mg/ml and 0.01 mg/ml, respectively, the relative activity to inhibit the cell growth being 51%, 39% and 27%.

EXAMPLE 14

Four grams of crude T.C.F.H obtained in the same manner as Example 12 was adsorbed on DEAE-cellulose (Whatman), and eluted with Tris-HCl buffer solution (pH: 7.0) at ion strength gradient from 0.03 M to 0.05 M to give five fractions.

The third fraction was subdivided in the same way as above to give four fractions, the second fraction of which was dialyzed with 0.02 M Tris buffer solution, desalted and freeze-dried, affording 9.1 mg of T.C.F.H.B as white powder.

From the fourth fraction (of the second DEAE-cellulose chromatography) was obtained 14.1 mg of T.C.F.H.A as white powder after dialysis with 0.02 M Tris buffer solution, followed by freeze drying.

The T.C.F.H.A and T.C.F.H.B isolated above each exhibited a single band when submitted to electrophoresis.

A tissue culture test on leukemia L1210 cells using the T.C.F.H.A showed that the relative survival rate (based on a control culture sample) after five days was 15%, the relative activity to inhibt the cell growth being 85%.

A similar test using the T.C.F.H showed a relative survival rate of 53% and a relative acitvity of 47% after five days at the same concentration.

EXAMPLE 15

The fourth fraction (70 mg), obtained from the second DEAE-cellulose chromatography in Example 14, was subjected to electrophoresis on polyacrylamide gel at pH 6.0 to isolate a single substance. Dialyis and freeze drying gave 11 mg of purified T.C.F.H.A as white powder.

EXAMPLE 16

Four grams of crude T.C.F.H obtained in the same manner as Example 12 was adsorbed on DEAE-cellulose (Whatman), and eluted with sodium chloride solution (pH: 7.0) at concentration gradient from 0.03 M to 0.01 M to give four fractions.

The third fraction was dialyzed, adsorbed on DEAE-cellulose (Whatman), and eluted with Tris-HCl buffer solution (pH: 7.0) at ion strength gradient from 0.03 M to 0.05 M to give four fractions.

The second fraction (of the second DEAE-cellulose chromatography) was dialyzed with 0.02 M Tris-HCl buffer solution, desalted and freeze-dried, affording 8.8 mg of T.C.F.H.B as white powder.

From the fourth fraction (of the second DEAE-cellulose chromatography) was obtained 13.7 mg of T.C.F.H.A as white powder after dialysis and freeze drying.

The T.C.F.H.A and T.C.F.H.B isolated above each exhibited a single band when submitted to electrophoresis.

These substances showed the same activities to inhibit the growth of cancer cells as Example 14.

EXAMPLE 17

The second fraction (40 mg), obtained from the second DEAE-cellulose chromatography in Example 14, was subjected to electrophoresis on polyacrylamide gel at pH 6.0 to isolate the effective component as a single substance. Dialyis and freeze drying gave 6.8 mg of purified T.C.F.H.B as white powder.

EXAMPLE 18

Tissue culture tests were conducted to determine the effect to inhibit the proliferation of various malignant tumor cells, for the T.C.F.H.A samples obtained in Examples 11, 12 and 14 (at 100 mcg/ml concentration).

For leukemia L5178Y cells, the survival rate after five days was 10.1%, the activity to inhibit the cell grow being 79.5%.

For sarcoma S180 cells, the survival rate after five days was 20.5%, the activity to inhibit the cell growth being 79.5%.

For Ehrlich's carcinoma cells, the survival rate after five days was 10.3%, the activity to inhibit the cell growth being 89.7%.

No such inhibitory effect was observed at all for the primary tissue-cultured cells of rat liver.

EXAMPLE 19

Tissue culture tests were conducted to determine the effect to inhibit the proliferation of various malignant tumor cells, for the T.C.F.H.B samples obtained in Examples 14 and 16 (at 100 mcg/ml concentration).

For leukemia L5178Y cells, the survival rate after five days was 61%, the activity to inhibit the cell growth being 39%.

For sarcoma S180 cells, the survival rate after five days was 83%, the activity to inhibit the cell growth being 17%.

For Ehrlich's carcinoma cells, the survival rate after five days was 72%, the activity to inhibit the cell growth being 28%.

No such inhibitory effect was observed at all for the primary tissue-cultured cells of rat liver.

EXAMPLE 20

An animal test was carried out using the purified T.C.F.H.A obtained in Example 15 from human clot to determine its effect upon ascites carcinoma. Three groups of male BDF$_1$ mice (weighing 20. g) were used for the test, each group consisting of five mice.

In the first group, 0.1 mg of T.C.F.H.A was abdominally administered to each mouse 24 hours after abdominal transplantation of leukemia L1210 cells ($1 \times 10^6$). Similarly, 0.01 mg of the sample was administered in the second group. The average life time was 9.3 days for the control group, 21.7 days for the first group, and 15.7 days for the second, the T/C value being 233% and 169% for the first and second groups, respectively.

EXAMPLE 21

An animal test was carried out using the purified T.C.F.H.B obtained in Example 7 from human clot to determine its effect upon ascites carcinoma. Three groups of male BDF$_1$ mice (weighing 20. g) were used for the test, each group consisting of five mice.

In the first group, 0.1 mg of T.C.F.H.B was abdominally administered to each mouse 24 hours after abdominal transplantation of leukemia L1210 cells ($1 \times 10^6$). Similarly, 0.01 mg of the sample was administered in the second group.

The average life time was 9.3 days for the control group, 14.7 days for the first group, and 13.0 days for the second, the T/C value being 158% and 140% for the first and second groups, respectively.

EXAMPLE 22

An animal test was conducted using the T.C.F.H.A obtained in Example 15 from human clot to determine its effect upon solid cancer.

Three groups of female ICR mice (weighing 20 g) were used for the test, each group consisting of five mice.

In the first group, 0.1 mg of T.C.F.H.A was hypodermically injected three times to each mouse—one day, three days and ten days after hypodermal injection of sarcoma 180 cells ($1 \times 10^7$) to the groin. The T.C.F.H.A was similarly administered to the second group, except that the amount applied each time was 0.01 mg.

In the control group, solid cancer averaging 4.5 g in weight was observed after 30 days. On the contrary, the average weight of solid cancer developed in the first and second groups was 0.9 g and 2.36 g, respectively, the reduction rate being 80% and 48%.

EXAMPLE 23

An animal test was conducted using the T.C.F.H.B obtained in Example 17 from human clot to determine its effect upon soild cancer.

Three groups of female ICR mice (weighing 20 g) were used for the test, each group consisting of five mice.

In the first group, 0.1 mg of T.C.F.H.B was hypodermically injected three times to each mouse—one day, three days and ten days after hypodermal injection of sarcoma 180 cells ($1 \times 10^7$) to the groin. The T.C.F.H.B was similarly administered to the second group, except that the amount applied each time was 0.01 mg.

In the control group, solid cancer averaging 4.5 g in weight was observed after 30 days. On the contrary, the average weight of solid cancer developed in the first and second groups was 2.33 g and 3.97 g, respectively, the reduction rate being 48% and 12%.

What we claim is:

1. A glycoprotein, fractionated from human blood or sera and named cancer-cell proliferation inhibitory factor A (T.D.F.H.A), which is a white powder melting at 245° to 249° C. (with decomposition); has a molecular weight of approximately 73,900 when measured by electrophoresis in 10% sodium dodecylsulfate solution; is readily soluble in water, and insoluble in butanol, acetone, ethyl acetate, chloroform, benzene and hexane; has an amino acid composition of 10.0% aspartic acid, 5.4% threonine, 3.8% serine, 16.0% glutamic acid, 4.2% proline, 1.4% glycine, 4.8% alanine, 2.6% cystine, 5.1% valine, 0.8% methionine, 2.2% isoleucine, 9.6% leucine, 4.9% tyrosine, 5.7% phenylalanine, 11.4% lysine, 3.5% histidine and 5.2% arginine in error of ±10% to the % values; shows a positive response to the ninhydrin, anthrone, Molish and periodic acid reactions; gives an infrared absorption spectrum as shown in FIG. 1 (KBr pellet); and exhibits ultraviolet absorption maxima at 279 nm in water of pH 3.0, at 278 nm in water of pH 7.0 and at 277 nm in water of pH 10.0, and is obtainable from the human body.

2. A protein having an action to inhibit the proliferation of malignant tumor cells, fractionated from human blood or sera and named cancer-cell proliferation inhibitory factor B (T.D.F.H.B), which is a white powder melting at 221° to 225° C. (with decomposition); has a molecular weight of approximately 22,100 when measured by electrophoresis in 10% sodium dodecylsulfate solution; is readily soluble in water, and insoluble in acetone, ethyl acetate, benzene, hexane and chloroform; has an amino acid composition of 16.0% aspartic acid, 5.2% threonine, 5.8% serine, 6.9% glutamic acid, 2.3% proline, 4.1% glycine, 5.9% alanine, 2.3% cystine, 4.4% valine, 1.7% methionine, 4.2% isoleucine, 7.9% leucine, 4.0% tyrosine, 3.9% phenylalanine, 7.7% lysine, 1.6% histidine and 11.6% arginine in error of ±10% to the values; shows a positive response to the ninhydrin reaction and a negative response to the anthrone, Molish and periodic acid reactions; gives an infrared absorption spectrum as shown in FIG. 5 (KBr pellet); and exhibits ultraviolet absorption maxima at 283 nm in water of pH 3.0, at 280 nm in water of pH 7.0 and at 277 nm in water of pH 10.0, and is obtainable from the human body.

3. A protein having an action to inhibit the proliferation of malignant tumor cells, fractionated from human blood or sera and named cancer-cell proliferation inhibitory factor C (T.D.F.H.C), which is a white powder melting at 237° to 240° C. (with decomposition); has a molecular weight of approximately 14,000 when measured by electrophoresis in 10% sodium dodecylsulfate solution; is readily soluble in water, and insoluble in acetone, ethyl acetate, benzene, hexane and chloroform; has an amino acid composition of 18.0% aspartic acid, 5.4% threonine, 6.4% serine, 5.2% glutamic acid, 1.7% proline, 5.1% glycine, 6.4% alanine, 2.1% cysteine, 4.3% valine, 1.9% methionine, 4.5% isoleucine, 6.8% leucine, 3.6% tyrosine, 3.0% phenylalanine, 6.0% lysine, 1.1% histidine and 11.6% arginine in error of ±10% to the % values; shows a positive response to the ninhydrin reaction and a negative response to the anthrone, Molish and periodic acid reactions; gives an infrared absorption spectrum as shown in FIG. 9 (KBr pellet); and exhibits ultraviolet absorption maxima at 278 nm in water of pH 3.0, at 290 nm in water of pH 7.0 and at 277 nm in water of pH 10.0, and is obtainable from the human body.

4. A protein having ability to inhibit the proliferation of malignant tumor cells, fractionated from human blood and named cancer-cell killing and proliferation inhibitory factor D (T.C.F.H.D), which is a white powder melting at 218° to 221° C. (with decomposition); has a molecular weight of approximately 40,000 when measured by electrophoresis in 10% sodium dodecylsulfate solution; is readily soluble in water, and insoluble in butanol, acetone, ethyl acetate, chloroform, benzene and hexane; has an amino acid composition of 8.9% aspartic acid, 5.7% threonine, 4.3% serine, 6.3% glutamic acid, 3.8% proline, 5.8% glycine, 5.8% alanine, 0.6% cysteine, 5.2% valine, 0.5% methionine, 2.2% isoleucine, 4.7% leucine, 3.0% tyrosine, 2.6% phenylalanine, 2.4% lysine, 1.3% histidine and 4.4% arginine in error of ±10% to the % values; shows a positive response to the ninhydrin reaction and a negative response to the anthrone, Molish and periodic acid reactions; gives an infrared absorption spectrum as shown in FIG. 13 (KBr pellet); and exhibits ultraviolet absorption maxima at 275 nm, 282.5 nm and 291.5 nm in water of pH 5.0, at 275 nm, 282.5 nm and 291.5 nm in water of pH 7.0, and at 282 nm and 291.5 nm in water of pH 10.0, and is obtainable from the human body.

5. A protein having ability to inhibit the proliferation of malignant tumor cells, fractionated from human blood and named cancer-cell killing and proliferation inhibiting factor E (T.C.F.H.E), which is a white powder melting at 231° to 233° C. (with decomposition); has a molecular weight of approximately 44,000 when measured by electrophoresis in 10% sodium dodecylsulfate solution; is readily soluble in water, and insoluble in acetone, ethyl acetate, chloroform, benzene and hexane; has an amino acid composition of 9.2% aspartic acid, 5.7% threonine, 4.3% serine, 8.6% glutamic acid, 4.0% proline, 4.7% glycine, 5.6% alanine, 1.0% cysteine, 5.2% valine, 0.6% methionine, 2.2% isoleucine, 6.0% leucine, 3.4% tyrosine, 3.1% phenylalanine, 4.4% lysine, 1.9% histidine and 4.7% arginine in error of ±10% to the % values; shows a positive response to the ninhydrin reaction and a negative response to the anthrone, Molish and periodic acid reactions; gives an infrared absorption spectrum as shown in FIG. 17 (KBr pellet); and exhibits ultraviolet absorption maxima at 280 nm (with a shoulder at 294 nm) in water of pH 5.0, at 280 nm (with a shoulder at 291 nm) in water of pH 7.0, and at 281 nm (with a shoulder at 293 nm) in water of pH 10.0, and is obtainable from the human body.

* * * * *